United States Patent
Fujioka

(10) Patent No.: US 12,344,871 B2
(45) Date of Patent: Jul. 1, 2025

(54) METHOD FOR PRODUCING CYSTEINE FROM GLUTATHIONE

(71) Applicants: AMANO ENZYME INC., Nagoya (JP); AMANO ENZYME EUROPE LTD., Oxfordshire (GB)

(72) Inventor: Hiroki Fujioka, Oxfordshire (GB)

(73) Assignees: AMANO ENZYME INC., Nagoya (JP); AMANO ENZYME EUROPE LTD., Oxfordshire (GB)

( * ) Notice: Subject to any disclaimer, the term of this patent is extended or adjusted under 35 U.S.C. 154(b) by 109 days.

(21) Appl. No.: 17/597,231

(22) PCT Filed: Jun. 17, 2020

(86) PCT No.: PCT/JP2020/023674
§ 371 (c)(1),
(2) Date: Dec. 29, 2021

(87) PCT Pub. No.: WO2021/002195
PCT Pub. Date: Jan. 7, 2021

(65) Prior Publication Data
US 2022/0243235 A1  Aug. 4, 2022

(30) Foreign Application Priority Data
Jul. 2, 2019 (JP) .................. 2019-124052

(51) Int. Cl.
| | | |
|---|---|---|
| C12N 9/78 | (2006.01) | |
| C12N 9/54 | (2006.01) | |
| C12N 9/62 | (2006.01) | |
| C12N 9/80 | (2006.01) | |
| C12P 13/12 | (2006.01) | |
| C12P 21/02 | (2006.01) | |

(52) U.S. Cl.
CPC .................. C12N 9/80 (2013.01); C12N 9/54 (2013.01); C12N 9/62 (2013.01); C12P 13/12 (2013.01); C12P 21/02 (2013.01); *C12Y 203/02002* (2013.01)

(58) Field of Classification Search
CPC .............. C12N 9/54; C12N 9/80; C12N 9/62
See application file for complete search history.

(56) References Cited

U.S. PATENT DOCUMENTS

2003/0138521 A1  7/2003  Nishimura et al.
2004/0265471 A1  12/2004  Kohmura et al.

FOREIGN PATENT DOCUMENTS

| JP | 2001-321117 A | 11/2001 |
|---|---|---|
| JP | 2001-321118 A | 11/2001 |
| JP | 4453057 B2 | 4/2010 |
| JP | 2018-033424 A | 3/2018 |
| WO | WO 00/030474 A1 | 6/2000 |
| WO | WO 2009/114954 A1 | 9/2009 |
| WO | WO 2009/152627 A2 | 12/2009 |

OTHER PUBLICATIONS

Ajinmoto. English Translation of JP 2001-321118 A Retrieved on Nov. 20, 2023.*
Li. Production of Taste Enhancers from Protein Hydrolysates of Porcine Hemoglobin and Meat Using Bacillus amyloliquefaciens Y-Glutamyltranspeptidase. Journal of Agricultural and Food Chemistry 2020 68 (42), 11782-11789.*
Yin. Purification and characterization of acidic protease from Aspergillus oryzae BCRC 30118. Journal of Marine Science and Technology, vol. 21, No. 1, pp. 105-110 (2013).*
International Search Report in PCT/JP2020/023674 issued Aug. 25, 2020.
Olson, C. K. and Binkley, Francis, "Metabolism of Glutathione, III. Enzymatic Hydrolysis of Cysteinylglycine," J. Biol. Chem. 1950, 186: 731-735.
Schroeder, E. F. and Woodward, Gladys E., "The Enzymatic Hydrolysis of Glutathione by Rat Kidney," J. Biol. Chem 1937, 120: 209-217.
Extended European Search Report received in counterpart European Patent Application No., 20835054.6, issued on Aug. 17, 2023.
Dal Degan F. et al., "Purification and characterization of two serine carboxypeptidases from Aspergillus niger and their use in C-terminal sequencing of proteins and peptide synthesis" Appl Environ Microbiol. Jul. 1992; 58(7):2144-2152.
European Office Action for European Application No. 20835054.6 dated Aug. 20, 2024 (in 8 pages).

* cited by examiner

Primary Examiner — Yong D Pak
(74) Attorney, Agent, or Firm — Knobbe, Martens, Olson & Bear, LLP

(57) ABSTRACT

It is an object of the present invention to provide a practical means of producing cysteine from glutathione that is also suitable for use in the field of foods. Cysteine is produced from glutathione by a first step of producing cysteinylglycine by the action of a γ-glutamyl peptidase derived from a microorganism on reduced glutathione; and a second step of producing cysteine by the action of an acid protease derived from a microorganism on the cysteinylglycine.

2 Claims, No Drawings

METHOD FOR PRODUCING CYSTEINE FROM GLUTATHIONE

TECHNICAL FIELD

The present invention relates to a method for producing cysteine from glutathione and applications thereof. The present application claims priority from Japanese Patent Application No. 2019-124052 filed on Jul. 2, 2019, the entire contents of which are herein incorporated by reference.

BACKGROUND ART

Amino acids and peptides in foods are important factors not only as nutrients but also for the taste and flavor of foods. For example, glutamate and aspartate have umami and sour tastes, glycine, alanine, threonine, and the like have a sweet taste, and tryptophan, isoleucine, valine, and the like have a bitter taste. Additionally, some amino acids react with other components (such as sugars and fat) to produce a unique flavor. One specific example is cysteine, and a Maillard reaction product of cysteine gives a meat flavor. For example, heat-treating a food or food material containing cysteine can enhance the umami taste. Likewise, adding cysteine to a food or the like and treating it similarly can also be expected to give or enhance the umami taste. However, cysteine is typically extracted from animal-derived raw materials (hair and feathers), and the use of cysteine as an additive in foods and the like is not favored.

Incidentally, some foods and the like are relatively rich in the cysteine compound glutathione. Therefore, if it is possible to produce cysteine from glutathione, the above-described problem with adding cysteine can be solved.

In the living body, glutathione undergoes stepwise enzymatic degradation (see, for example, Non Patent Literatures 1 and 2), specifically as follows: First, γ-glutamyl transpeptidase cleaves the γ-glutamyl bond of glutathione into glutamate (Glu) and the dipeptide cysteinylglycine (CysGly). CysGly is then degraded by dipeptidases into cysteine (Cys) and glycine (Gly). If it is possible to apply this two-step degradation in the living body to foods and the like, cysteine can be produced from the component (glutathione) originally contained in foods and the like to give a flavor or enhance the flavor. A technique related to the first-step reaction has been proposed, which enhances the flavor of foods and the like by producing CysGly from glutathione using a glutaminase derived from a microorganism (Patent Literature 1). Regarding the second-step reaction, reports have been made on the degradation of CysGly by enzymes derived from animals (for example, derived from rat, rabbit, pig, or horse) (Non Patent Literatures 1 and 2). However, animal-derived enzymes are difficult to apply to foods and the like. There exists no case in which CysGly is successfully degraded by an enzyme suitable for use in the field of foods.

CITATION LIST

Patent Literature

Patent Literature 1: Japanese Patent No. 4453057

Non Patent Literature

Non Patent Literature 1: J. Biol. Chem. 1950, 186:731-735.

Non Patent Literature 2: J. Biol. Chem. 1937, 120:209-217.

SUMMARY OF INVENTION

Technical Problem

While the production of cysteine from glutathione, originally present in foods and the like is a promising means of giving a flavor to or enhancing the flavor of foods and the like, it is yet to be realized. In view of this situation, it is an object of the present invention to provide a practical cans of producing cysteine from glutathione that is also suitable for use in the field of foods (food applications).

Solution to Problem

With the above-described object, the present inventors have conducted extensive studies with a view toward efficiently producing cysteine from glutathione using enzymes derived from microorganisms, while contemplating the use in the field of foods. As a result, the inventors have successfully produced cysteine from glutathione efficiently by using a combination of a glutaminase, which is one of γ-glutamyl peptidases, and an acid protease. The inventors have also found particularly effective reaction conditions and useful information for realizing practical use. The following invention is provided based on these results.

[1] A method for producing cysteine from glutathione comprising:
  a first step of producing cysteinylglycine by the action of a γ-glutamyl peptidase derived from a microorganism on reduced glutathione; and
  a second step of producing cysteine by the action of an acid protease derived from a microorganism on the cysteinylglycine.

[2] The method according to [1], wherein the first step is performed by adding the γ-glutamyl peptidase derived from a microorganism and the acid protease derived from a microorganism to a glutathione-containing composition or a solution thereof, or a glutathione solution, and then carrying out the reaction at a pH of 3 to 9 and a temperature of 15 to 70° C.; and subsequently, the second step is performed by adjusting the reaction solution to a pH of 2 to 7, and carrying out the reaction at a temperature of 20 to 70° C.

[3] The method according to [1], wherein the first step is performed by adding the γ-glutamyl peptidase derived from a microorganism to a glutathione-containing composition or a solution thereof, or a glutathione solution, and then carrying out the reaction at a pH of 3 to 9 and a temperature of 15 to 70° C.; and subsequently, the second step is performed by adding the acid protease derived from a microorganism to the reaction solution, and carrying out the reaction at a pH of 2 to 7 and a temperature of 20 to 70° C.

[4] The method according to claim 1, wherein the first step and the second step are performed by adding the γ-glutamyl peptidase derived from a microorganism and the acid protease derived from a microorganism to a glutathione-containing composition or a solution thereof, or a glutathione solution, and then carrying out the reaction at a pH of 3 to 6 and a temperature of 15 to 70° C.

[5] The method according to [2] or [3], wherein reaction conditions for the first step are a pH of 4 to 8 and a temperature of 30 to 60° C., and reaction conditions for the second step are a pH of 3 to 6 and a temperature of 20 to 60° C.

[6] The method according to [2] or [3], wherein reaction conditions for the first step are a pH of 5 to 7 and a temperature of 30 to 50° C., and reaction conditions for the second step are a pH of 3 to 5 and a temperature of 30 to 50° C.

[7] The method according to any one of [1] to [6], wherein the γ-glutamyl peptidase derived from a microorganism is a glutaminase, a γ-glutamyl transferase, or a γ-glutamylcyclotransferase.

[8] The method according to any one of [1] to [6], wherein the γ-glutamyl peptidase derived from a microorganism is a glutaminase derived from a microorganism of the genus *Bacillus*.

[9] The method according to any one of [1] to [6], wherein the γ-glutamyl peptidase derived from a microorganism is a glutaminase derived from *Bacillus amyloliquefaciens*.

[10] The method according to any one of [1] to [9], wherein the acid protease derived from a microorganism is an acid protease derived from a microorganism of the genus *Aspergillus*.

[11] The method according to any one of [1] to [9], wherein the acid protease derived from a microorganism is an acid protease derived from *Aspergillus oryzae*.

[12] The method according to any one of [1] to [11], wherein the glutathione-containing composition is meat, a processed meat product, seafood, a processed seafood product, a vegetable, a processed vegetable product, yeast extract, or meat extract.

DESCRIPTION OF EMBODIMENTS

The present invention relates to a method for producing cysteine from glutathione (also referred to as the "cysteine production method of the present invention"). The cysteine production method of the present invention is highly versatile, and can be used for the purpose of, for example, producing cysteine from glutathione present in foods or food materials, or obtaining cysteine from purified or crude glutathione. As described below, targets to be treated (materials to be treated) in the present invention include foods or food materials containing glutathione, and a glutathione solution. Glutathione in the material to be treated may be in a form (for example, reduced form) capable of being at least partially degraded by an enzyme (γ-glutamyl peptidase derived from a microorganism) used in the present invention.

The cysteine production method of the present invention uses roughly two types of enzymes to produce cysteine from glutathione by a two-step cleavage and degradation reaction. Specifically, cysteine is produced from glutathione by the step (first step) of producing cysteinylglycine by the action of a γ-glutamyl peptidase derived from a microorganism on reduced glutathione; and the step (second step) of producing cysteine by the action of an acid protease derived from a microorganism on the cysteinylglycine produced.

The first step involves the reaction in which the γ-glutamyl bond of reduced glutathione is cleaved by the action of the γ-glutamyl peptidase derived from a microorganism to produce cysteinylglycine (CysGly) (glutamate is also produced as a by-product). The γ-glutamyl peptidase derived from a microorganism is not limited as long as it can achieve cleavage of the γ-glutamyl bond of reduced glutathione. Examples of the γ-glutamyl peptidase derived from a microorganism include a glutaminase derived from a microorganism of the genus *Bacillus*, a γ-glutamyl transferase, and a γ-glutamylcyclotransferase. One example of the glutaminase derived from a microorganism of the genus *Bacillus* is a glutaminase derived from *Bacillus amyloliquefaciens* (for example, Glutaminase SD-C100S offered by Amano Enzyme Inc.). The γ-glutamyl peptidase derived from a microorganism may not necessarily be purified, and may be, for example, a culture or a homogenate/an extract of a microorganism that produces γ-glutamyl peptidase, or a partially purified product thereof. Two or more γ-glutamyl peptidases derived from microorganisms may be used in combination. Several γ-glutamyl peptidases derived from microorganisms are commercially available (for example, Glutaminase SD-C100S mentioned above), and can be readily obtained and used.

The second step involves the reaction in which CysGly produced in the first step is degraded by the action of the acid protease derived from a microorganism to produce cysteine (glycine is also produced as a by-product). The acid protease derived from a microorganism is not limited as long as it can achieve degradation of CysGly. One example of the acid protease derived from a microorganism is an acid protease derived from a microorganism of the genus *Aspergillus*. Examples of the acid protease derived from a microorganism of the genus *Aspergillus* include an acid protease derived from *Aspergillus oryzae* (for example, Protease M "Amano" SD and Protease HF "Amano" 150SD offered by Amano Enzyme Inc.). The acid protease derived from a microorganism may not necessarily be purified, and may be, for example, a culture or a homogenate/an extract of a microorganism that produces acid protease, or a partially purified product thereof. Two or more acid proteases derived from microorganisms may be used in combination. Several acid proteases derived from microorganisms are commercially available (for example, Protease M "Amano"SD and Protease HF "Amann" 150S mentioned above), and can be readily obtained and used.

In the present invention, it is required that a state in which the first step is followed by the second step be formed in the entire process. Thus, in one embodiment (first embodiment) of the present invention, the first step is performed by adding the γ-glutamyl peptidase derived from a microorganism and the acid protease derived from a microorganism to a glutathione-containing composition or a solution thereof, or a glutathione solution, and then carrying out the reaction under conditions in which the γ-glutamyl peptidase derived from a microorganism acts (referred to as the "first conditions"); and subsequently, the second step is performed by changing the conditions to conditions in which the acid protease derived from a microorganism acts (referred to as the "second conditions"), and carrying out the reaction. This embodiment eliminates the need to add an enzyme (acid protease derived from a microorganism) during the process, which improves workability.

The glutathione-containing composition or a solution thereof is used as one material to be treated. Examples of the glutathione-containing composition include, but are not limited to, foods or food materials containing glutathione. The term "food material" is to be interpreted in a broad sense, and includes natural food materials, such as meat, fish, and vegetables, as well as processed products or extracts thereof, and seasonings. Specific examples of foods and food materials include meat, processed meat products, seafood, processed seafood products, vegetables, processed vegetable products, yeast extract, and meat extract.

Besides the glutathione-containing composition or a solution thereof, the glutathione solution is also a material to be treated in the present invention. Typically, the glutathione solution is prepared by dissolving glutathione in a suitable solvent (for example, water). Glutathione is produced by extraction from yeast, organic synthesis, or the like, and is offered (commercially available) as a reagent, a drug, a pharmaceutical ingredient, or the like. As described above, glutathione in the material to be treated needs to be at least partially in reduced form, and the glutathione solution is typically prepared using reduced glutathione.

The conditions in which the γ-glutamyl peptidase derived from a microorganism acts, i.e., the first conditions, are, for example, a pH of 3 to 9 and a reaction temperature of 15 to 70° C. The pH is preferably 4 to 8, and more preferably 5 to 7. The reaction temperature is preferably 30 to 60° C., and more preferably 30 to 50° C. The reaction time and the amount of enzyme are not limited as long as the expected effect is achieved. For example, the reaction time may be from 5 minutes to 48 hours. The amount of enzyme is such that the concentration of the γ-glutamyl peptidase derived from a microorganism in the reaction solution is, for example, 0.001% (W/W) to 10% (W/W), preferably 0.01% (W/W) to 1% (W/W). Particularly preferred reaction conditions when using the glutaminase derived from *Bacillus amyloliquefaciens* as the γ-glutamyl peptidase derived from a microorganism are a pH of 5 to 7 and a reaction temperature of 35 to 45° C.

The conditions in which the acid protease derived from a microorganism acts, i.e., the second conditions, are, for example, a pH of 2 to 7 and a reaction temperature of 20 to 70° C. The pH is preferably 3 to 6, and more preferably 3 to 5. The reaction temperature is preferably 20 to 60° C., and more preferably 30 to 50° C. The reaction time and the amount of enzyme are not limited as long as the expected effect is achieved. For example, the reaction time may be from 5 minutes to 12 hours. If the reaction time is long, oxidation of the cysteine produced may occur, and thus, it is preferred to increase the reaction efficiency by, for example, increasing the amount of enzyme, and optimizing the reaction conditions (particularly the pH and temperature). The amount of enzyme is such that the concentration of the acid protease derived from a microorganism in the reaction solution is, for example, 0.001% (W/W) to 10% (W/W), preferably 0.01% (W/W) to 2% (W/W). Particularly preferred reaction conditions when using the acid protease derived from *Aspergillus oryzae* as the acid protease derived from a microorganism are a pH of 3 to 5 and a reaction temperature of 30 to 50° C.

To change the first conditions to the second conditions, the pH of the reaction solution may typically be adjusted using an acid (for example, hydrochloric acid, sulfuric acid, nitric acid, or acetic acid) or an alkali (for example, sodium hydroxide, potassium hydroxide, sodium carbonate, potassium carbonate, calcium hydroxide, or magnesium hydroxide).

The cysteine produced is recovered or purified, as required. For example, when the glutathione solution is used as the material to be treated, recovery/purification is carried out to obtain cysteine with high purity. Recovery/purification may be carried out using, for example, column chromatography.

In another embodiment (second embodiment) of the present invention, the first step is performed by adding the γ-glutamyl peptidase derived from a microorganism to a glutathione-containing composition or a solution thereof, or a glutathione solution, and then carrying out the reaction under conditions in which the γ-glutamyl peptidase derived from a microorganism acts (referred to as the "first conditions"); and subsequently, the second step is performed by adding the acid protease derived from a microorganism to the reaction solution, and carrying out the reaction under conditions in which the acid protease derived from a microorganism acts (referred to as the "second conditions"). In this embodiment, the acid protease derived from a microorganism is not present in the reaction solution during the first step (cleavage of the γ-glutamyl bond by the γ-glutamyl peptidase derived from a microorganism), and there is no possibility that the γ-glutamyl peptidase derived from a microorganism is degraded (digested) by the acid protease derived from a microorganism. Thus, satisfactory or efficient cleavage of the γ-glutamyl bond by the γ-glutamyl peptidase derived from a microorganism can be expected. The first conditions and the second conditions in the second embodiment are the same as the above-described first conditions and second conditions, respectively, in the first embodiment. The reaction time and the amount of enzyme are also the same.

In still another embodiment (third embodiment) of the present invention, the γ-glutamyl peptidase derived from a microorganism and the acid protease derived from a microorganism are added to a glutathione-containing composition or a solution thereof, or a glutathione solution, and then the reaction is carried out under conditions in which both the γ-glutamyl peptidase derived from a microorganism and the acid protease derived from a microorganism can act. That is, the first and second steps are carried out simultaneously. This embodiment eliminates the need to add an enzyme during the process, and also eliminates the need to change the reaction conditions, which improves workability. The conditions in which the γ-glutamyl peptidase derived from a microorganism and the acid protease derived from a microorganism can act simultaneously are, for example, a pH of 3 to 6 and a reaction temperature of 20 to 70° C. The pH is preferably 4 to 6. The reaction temperature is preferably 20 to 60° C., and more preferably 30 to 50° C. The reaction time and the amount of enzyme are not limited as long as the expected effect is achieved. For example, the reaction time may be from 5 minutes to 24 hours. If the reaction time is long, oxidation of the cysteine produced may occur, and thus, it is preferred to increase the reaction efficiency by, for example, increasing the amount of enzyme, and optimizing the reaction conditions (particularly the pH and temperature).

Examples

The following experiments were carried out with a view toward establishing a method for efficiently producing cysteine from glutathione, while contemplating the use in the field of foods.

1. Study on Cysteine Production Using Single Enzyme Treatment (1) Method 0.020 mL of a 5% (w/v) enzyme solution was added to 1.0 mL of 50 mmol/L reduced glutathione, and the mixture was allowed to stand at 37° C. for 16 hours to carry out the reaction; thereafter, the reaction solution was analyzed by HPLC. The amount of cysteine produced was evaluated based on the ratio of the peak area of L-cysteine to the total peak area. The enzymes used are shown in the following table (Table 1).

TABLE 1

| Product Name | Enzyme |
| --- | --- |
| Glutaminase SD-C100S | Glutaminase derived from *Bacillus amyloliquefaciens* |

TABLE 1-continued

| Product Name | Enzyme |
|---|---|
| Peptidase R | Peptidase derived from *Rhizopus oryzae* |
| Protease A "Amano" SD | Neutral peptidase derived from *Aspergillus oryzae* |
| ProteaAX | Peptidase derived from *Aspergillus oryzae* |
| Protease M "Amano" SD | Acid protease derived from *Aspergillus oryzae* |
| Protease P "Amano" 6SD | Alkaline peptidase derived from *Aspergillus melleus* |
| Protease HF "Amano" 150SD | Acid protease derived from *Aspergillus oryzae* |

(2) Results

The single enzyme treatment produced almost no L-cysteine (Table 2).

TABLE 2

| Enzyme Used | Reaction pH | Amount (%) of Cysteine Produced |
|---|---|---|
| None | pH7 | 0.3 |
| Glutaminase SD-C100S | | 0.4 |
| Peptidase R | | 0.5 |
| Protease A "Amano" SD | | 0.5 |
| ProteaAX | | 0.4 |
| Protease M "Amano" SD | | 0.4 |
| Protease P "Amano" 6SD | | 0.4 |
| Protease HF "Amano" 150SD | pH4 | 0.0 |

2. Study on Cysteine Production Using Combinations of Glutaminase and Various Enzymes (1) Method 0.02 mL of a 5% (w/v) enzyme solution was added to 1.0 mL of 50 mmol/L reduced glutathione (pH 4, 5, 6, or 7), and the mixture was allowed to stand at 37° C. for 12 hours to carry out the reaction; thereafter, the reaction solution was analyzed by HPLC. The amount of cysteine produced was evaluated based on the ratio of the peak area of L-cysteine to the total peak area.

(2) Results

The combinations of glutaminase and acid proteases resulted in efficient production of cysteine at pH 4 to 6 (Table 3).

TABLE 3

| Enzyme Used | Reaction pH | Amount (%) of Cysteine Produced |
|---|---|---|
| None | pH7 | 0.3 |
| Glutaminase SD-C100S | | 0.3 |
| Glutaminase SD-C100S + Peptidase R | | 1.9 |
| Glutaminase SD-C100S + Protease A "Amano" SD | | 2.8 |
| Glutaminase SD-C100S + ProteaAX | | 2.0 |
| Glutaminase SD-C100S + Protease M "Amano" SD | | 1.9 |
| Glutaminase SD-C100S + Protease P "Amano" 6SD | | 1.0 |
| None | pH6 | 0.3 |
| Glutaminase SD-C100S | | 0.3 |
| Glutaminase SD-C100S + Protease M "Amano" SD | | 10.9 |
| Glutaminase SD-C100S + Protease HF "Amano" 150SD | | 16.5 |
| None | pH5 | 0.3 |
| Glutaminase SD-C100S | | 0.3 |

TABLE 3-continued

| Enzyme Used | Reaction pH | Amount (%) of Cysteine Produced |
|---|---|---|
| Glutaminase SD-C100S + Protease M "Amano" SD | | 20.5 |
| Glutaminase SD-C100S + Protease HF "Amano" 150SD | | 28.8 |
| None | pH4 | 0.3 |
| Glutaminase SD-C100S | | 0.3 |
| Glutaminase SD-C100S + Protease M "Amano" SD | | 32.2 |
| Glutaminase SD-C100S + Protease HF "Amano" 150SD | | 25.8 |

3. Study on Treatment Conditions (1) Method 0.8 mL of a 5% (w/v) glutaminase solution was added to 40 mL of 50 mmol/L reduced glutathione (pH 6.0), and the mixture was allowed to stand at 37° C. for 12 hours to carry out the reaction. The reaction solution was subsequently adjusted to pH 4.0 with hydrochloric acid, and adjusted to a volume of 50 mL; then, protease HF "Amann" 150SD was added to give a final concentration of 0.5% (w/v) or 2.0% (w/v), and the mixture was allowed to stand at 37 or 50° C. for 4 to 24 hours to carry out the reaction; thereafter, the reaction solution was analyzed by HPLC. The amount of cysteine produced was evaluated based on the ratio of the peak area of L-cysteine to the total peak area.

(2) Results

The greater the amount of the protease, the faster the cysteine production. Furthermore, the amount of cysteine produced increased more when the reaction was carried out at 50° C. than at 37° C. (Table 4).

TABLE 4

| Reaction Temperature | Protease Concentration | Reaction Time (h) | Amount (%) of Cysteine Produced |
|---|---|---|---|
| 37° C. | 0% | 4 | 0.2 |
| | | 8 | 0.2 |
| | | 24 | 0.7 |
| | 0.5% | 4 | 7.6 |
| | | 8 | 11.8 |
| | | 24 | 18.9 |
| | 2.0% | 4 | 22.0 |
| | | 8 | 26.9 |
| | | 24 | 22.9 |
| 50° C. | 0% | 4 | 0.2 |
| | | 8 | 0.2 |
| | | 24 | 0.0 |
| | 0.5% | 4 | 9.2 |
| | | 8 | 14.5 |
| | | 24 | 19.5 |
| | 2.0% | 4 | 28.2 |
| | | 8 | 29.0 |
| | | 24 | 22.0 |

4. Study on Yield Improvement (1) Method 100 mg of Glutaminase SD-C100S and 400 mg of Protease HF "Amann" 150SD were added to 9 mL of 0.153 g (w/v) reduced glutathione (pH 6.0) (final concentration 50 mM), and the mixture was allowed to stand at 37° C. for 3 hours to carry out the reaction; thereafter, the reaction solution was adjusted to pH 4.0, and further allowed to stand at 37 or 50° C. for 3 hours to carry out the reaction. The reaction solution was analyzed by HPLC, and the concentration of L-cysteine produced was calculated.

(2) Results

About 40 mM of cysteine was produced from 50 mM of reduced glutathione (Table 5). While sufficient amount of cysteine was also produced when the reaction temperature after the adjustment to pH 4.0 was set to 50° C., the amount of cysteine produced decreased slightly compared to that at 37° C. It is assumed that the oxidation of SH groups occurred due to the high-temperature reaction, which caused the concentration to decrease.

TABLE 5

| Reaction Temperature | Amount (mM) of Cysteine Produced |
|---|---|
| 37° C. | 40.2 |
| 50° C. | 35.4 |

INDUSTRIAL APPLICABILITY

The present invention is useful for increasing the amount of cysteine in foods or food materials, for example. In other words, in accordance with the present invention, foods or food materials with an increased cysteine content can be produced. Thus, the present invention can also be interpreted as a method for producing a composition (for example, a food or a food material) with an increased cysteine content. Besides increasing the amount of cysteine in foods or food materials, the present invention can also be used for the purpose of obtaining cysteine from purified or crude glutathione. Therefore, the present invention is highly versatile, and is expected to be used in a variety of fields.

This invention is in no way limited to the foregoing description of the embodiments of the invention and examples. This invention also includes various modifications that would be readily devised by those skilled in the art, without departing from the scope of the claims. All articles, unexamined patent application publications, and patent application publications expressly indicated herein are entirely incorporated by reference.

The invention claimed is:

1. A method for producing cysteine from glutathione comprising:
    adding a glutaminase derived from *Bacillus amyloliquefaciens* and an acid protease derived from *Aspergillus oryzae* to a glutathione-containing composition or a solution thereof, or a glutathione solution;
    a first step of producing cysteinylglycine by reacting the glutaminase derived from *Bacillus amyloliquefaciens* on the glutathione-containing composition or a solution thereof, or a glutathione solution to produce cysteinylglycine; and
    a second step of producing cysteine by reacting the acid protease derived from *Aspergillus oryzae* on the cysteinylglycine,
    wherein the first step and the second step are simultaneously performed, and wherein the first and second reactions are carried out at a pH of 4 to 6.

2. The method according to claim 1, wherein the glutathione-containing composition is meat, a processed meat product, seafood, a processed seafood product, a vegetable, a processed vegetable product, yeast extract, or meat extract.

* * * * *